US008394410B2

(12) United States Patent
Domb et al.

(10) Patent No.: US 8,394,410 B2
(45) Date of Patent: Mar. 12, 2013

(54) SOFT POLYLACTIDES

(75) Inventors: Abraham J. Domb, Efrat (IL); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 413 days.

(21) Appl. No.: 11/335,138

(22) Filed: Jan. 19, 2006

(65) Prior Publication Data

US 2007/0036855 A1 Feb. 15, 2007

Related U.S. Application Data

(60) Provisional application No. 60/645,440, filed on Jan. 20, 2005.

(51) Int. Cl.
*A61K 9/14* (2006.01)

(52) U.S. Cl. ........................................................ 424/486

(58) Field of Classification Search ........................ None
See application file for complete search history.

(56) References Cited

U.S. PATENT DOCUMENTS

| | | | | |
|---|---|---|---|---|
| 4,728,721 | A | 3/1988 | Yamamoto et al. | |
| 5,578,325 | A | 11/1996 | Domb et al. | |
| 6,136,333 | A | 10/2000 | Cohn et al. | |
| 6,692,728 | B2 | 2/2004 | Weipert et al. | |
| 2002/0172646 | A1* | 11/2002 | Weipert et al. | 424/59 |
| 2003/0175222 | A1 | 9/2003 | Weipert et al. | |
| 2004/0157963 | A1* | 8/2004 | Brown et al. | 524/47 |

FOREIGN PATENT DOCUMENTS

| | | |
|---|---|---|
| EP | 0 644 219 | 3/1995 |
| WO | WO 98/01493 | 1/1998 |

OTHER PUBLICATIONS

Gref, et al., *Advanced Drug Delivery Reviews*, 16:215-233 (1995).

* cited by examiner

*Primary Examiner* — Paul Dickinson

(74) *Attorney, Agent, or Firm* — Pabst Patent Group LLP

(57) ABSTRACT

Biodegradable polymeric compositions that are liquids or pastes at temperatures below 37° C. are described. Immersion of the compositions in aqueous medium, such as body fluids, increases the viscosity of the composition resulting in the formation of a semisolid material. The polymeric material is a hydroxyalkanoic acid polyester derived from the copolymerization of at least one unsaturated hydroxy fatty acid copolymerized with hydroxyalkanoic acids of 2-6 carbons.

16 Claims, 4 Drawing Sheets

1.
2.
3.
Temperature (°C)
0
50
100
150
200
(a)
(b)
(c)
(d)
(e)
(f)
162°C
147°C
142°C
111°C
93°C
87°C
160.5°C
159°C
143°C
140°C
137°C

SOFT POLYLACTIDES

CROSS-REFERENCE TO RELATED APPLICATION

This application claims priority to U.S. Ser. No. 60/645,440 entitled "Hydrophobic Polyester of Hydroxyalkanoic Acids and Hydroxyl Fatty Acids", which was filed on Jan. 20, 2005.

FIELD OF THE INVENTION

The present invention is concerned with the preparation of biodegradable polymers, particularly polyhydroxyalkanoic acid polyesters, which form an in situ implant for the release of one or more active agents.

BACKGROUND OF THE INVENTION

Biodegradable matrices for drug delivery are useful because they obviate the need to remove non-degradable drug depleted devices. Many biodegradable polymers have been evaluated for their suitability for use as a matrix for drug delivery. Examples include polyesters, polycarbonates, natural and synthetic polyamides, polyphosphate esters, polyphosphazenes and polyanhydrides.

Polyanhydrides have been used as bioabsorbable materials for controlled drug delivery. Polyanhydrides degrade to dicarboxylic acid monomers when placed in aqueous medium. Several review articles have been published on polyanhydrides for controlled drug delivery applications. However, these polymers degrade in a short period, typically less than 20 weeks.

Linear polyesters of lactide and glycolide have been used for more than three decades for a variety of medical applications, including delivery of drugs. (Handbook of Biodegradable Polymers, A. Domb, J. Kost and D. Wiseman, Harwood and Brooks (1997). PLA has wide applications in medicine because of its biocompatibility and degradability into non-toxic products. Micelles and particles of the AB block copolymer poly(lactide)-b-poly(ethyleneglycol) (PLA-b-PEG) have received attention for use in intravenous injectable delivery systems for extended and targeted drug release (Gref et al., Protein Delivery-Physical Systems, L. M. Sanders and H. Hendren, Eds, Plenum Press, (1997); and Gref et al., Advanced Drug Delivery Reviews, 16: 215-233 (1995)). Similarly, U.S. Pat. No. 5,578,325 to Domb et al. describes multiblock copolymers comprising a multifunctional compound covalently linked with one or more hydrophilic polymers and one or more hydrophobic bioerodible polymers and including at least three polymer blocks. A PEG-coating on a microparticle or other polymeric device prevents the adsorption of plasma proteins and fast elimination by the reticulo endothelial system (RES).

Several liquid polymer formulations that change their viscosity have been reported including a temperartue sensitive aqueous solution of a copolymer of poly(lactic acid) [PLA] with polyethylene glycole [PEG] which is liquid at 15° C. but form a gel at temperatures above 30° C. such as when injected in the body. This system uses a solvent, water, thus forming a hydrophilic gel upon injection in tissue.

The ideal polymeric matrix for controlled drug delivery would have the characteristics of a biodegradable, solvent-free liquid or paste material that allows easy mixing in of bioactive agents to form a depot of drug at the site of injection. The desired polymeric material should be an injectable liquid or paste at room temperature while rapidly increase its viscosity shortly after injection in tissue so that it remain in the site of injection while releasing the incorporated active agents for an extended time period.

Such a polymer must be hydrophobic so that it retains its integrity and the incorporated drug for a suitable period of time when placed in biological systems, such as the body, and stable under common storage conditions, preferable room temperature, for an extended periods before use.

Fatty acids are suitable candidates for the preparation of biodegradable polymers, as they are natural body components and are hydrophobic, thus allowing retention of an encapsulated drug for longer periods of time when used for drug delivery. However, most fatty acids are monofunctional and cannot serve as monomers for polymerization. The use of functionalized fatty acids has been described in order to overcome this limitation. For example, very low molecular weight copolymers of lactic acid and ricinoleic acid prepared from crude (<88% pure) lactic acid and ricinoleic acid for use in cosmetics has been reported in U.S. Pat. No. 6,692,728 to Weipert et al.

In spite of the previously described drug delivery systems, there is still a need for a reliable polymer composition that can be injected into the body where it forms an in situ implant for the controlled release of drugs or serves as a temporary surgical implant.

It is therefore an object of the invention to provide biodegradable polyesters that are liquids or pastes at temperatures below 37° C. that allows the incorporation of active agents without the use of solvents or heat, methods of making the polyesters thereof and methods of use.

BRIEF SUMMARY OF THE INVENTION

Biodegradable polymeric compositions that are liquids or pastes at temperatures below 37° C. are described. Immersion of the compositions in aqueous medium, such as body fluids, increases the viscosity of the composition resulting in the formation of a semisolid material. The polymeric material is a hydroxyalkanoic acid polyester derived from the copolymerization of at least one unsaturated hydroxy fatty acid copolymerized with hydroxyalkanoic acids of 2-6 carbons.

DETAILED DESCRIPTION OF THE INVENTION

I. Composition a. Polyhydroxyalkanoic Acid Polyesters

Figure 1:
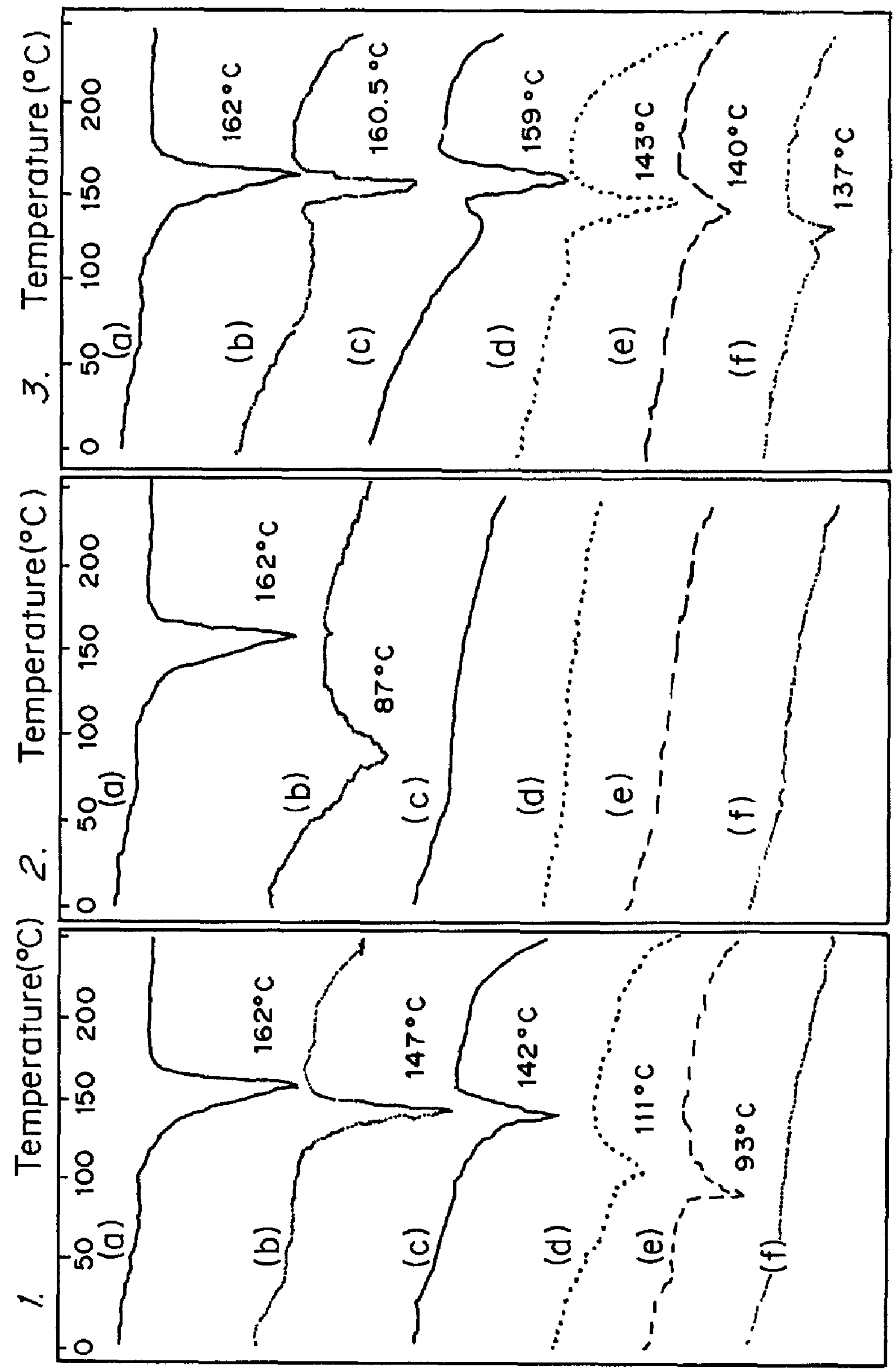
FIG. 1 shows the crystalline structure, as determined by DSC, for polyhydroxyalkanoic acid polyesters synthesized by transesterification and ring-opening polymerization (ROP): (a) 100% PLA; (b) P(LA-RA) 90:10 w/w; (c) P(LA-RA) 80:20 w/w; (d) P(LA-RA) 70:30 w/w; (e) P(LA-RA) 60:40 w/w; (f) P(LA-RA) 50:50 w/w.

Polyhydroxyalkanoic acid polyesters are derived from the copolymerization of at least one unsaturated hydroxy fatty acid with a hydroxyalkanoic acid.

The hydroxyalkanoic acid preferably has from 2-6 carbon atoms. Suitable hydroxyalkanoic acids include, but are not limited to, lactic acid, glycolic acid, 4-hydroxybutanoic acid, and 5-hydroxypentanoic acid. In a preferred embodiment, the hydroxyalkanoic acid is lactic acid. Enantiomerically pure PLA is a semi-crystalline polymer with $T_g$ of about 55° C. and $T_m$ of about 180° C. The degree of crystallinity and the melting point of PLA polymers can be reduced by random copolymerization with other comonomers, which leads to the disturbance of the crystallization ability of the PLA segments. For example, glycolide, ϵ-caprolactone, δ-valerolactone, 1,5-dioxepan-2-one (DXO) and trimethylene carbonate (TMC) are frequently used as comonomers in order to change the thermal properties of PLA.

In a preferred embodiment, the unsaturated hydroxy fatty acid is ricinoleic acid. Ricinoleic acid is a common $C_{18}$ fatty acid with a cis-configured double bond at the 9 position and a hydroxyl group at the 12 position (cis-12-hydroxyoctadeca-9-enoic acid). It is produced from the hydrolysis of castor oil and it is available as castor oil hydrolizate with a ricinoleic acid content of up to 85% and the remainder being mostly monocarboxylic acids such as oleic and stearic acid as well as other components.

b. Agents to be Incorporated into the Polymer Matrix

Any therapeutic, prophylactic or diagnostic agent can be incorporated into matrix. Agents that can be incorporated into the polymer include, but are not limited to, naleptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents, antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; beta-agonist; tocolytic agents and combinations thereof.

An effective amount of these agents can be determined by one of ordinary skill in the art. Factors to consider in determining a therapeutically effective amount include age, weight and physical condition of the person to be treated; type of agent used, type of polymer used; and desired release rate. Typically, between about 0.01% (w/w/) and 80% (w/w), more typically between 0.1 and 20-50% (w/w) of the active agent is incorporated into the polymer.

c. Excipients

The agent may be incorporated alone or with standard excipients, such as surfactants, plasticizers, pigments, colorants, stabilizing agents, glidants, etc. The formulation may also be coated with a sustained or delayed release coating and/or an enteric coating in the case of oral formulations. A plasticizer is normally present to reduce the fragility of the coating, and will generally represent about 10 wt. % to 50 wt. % relative to the dry weight of the polymer. Examples of typical plasticizers include, but are not limited to, polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

II. Method of Making a. Polyhydroxyalkanoic Acid-Fatty Acid Copolyesters

Copolyesters based on purified ricinoleic (RA) and lactic (LA) acids with different RA:LA ratios were synthesized by (a) thermal polycondensation; and (b) transesterification of high molecular weight poly(lactic acid) with ricinoleic acid and repolymerization. These methods are described in Scheme 1. Thermal polycondensation resulted in random P(LA-RA) copolyesters of molecular weights between 3,000 and 20,000. Polymers containing 20% or more RA were liquids at room temperature. $^1$H-NMR spectroscopy analysis coupled with information from DSC allowed determination of the polymer structure.

a. Thermal Polycondensation

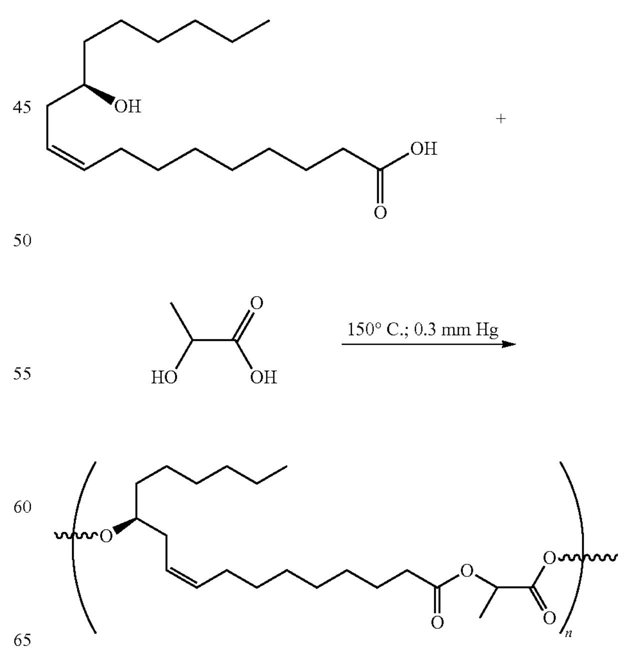

b. Transesterification and Re-Esterification

Scheme 1.

Synthesis of poly (RA-LA) by: (a) random condensation of LA and RA acids; (b) transesterification of PLA with RA and re-polyesterification.

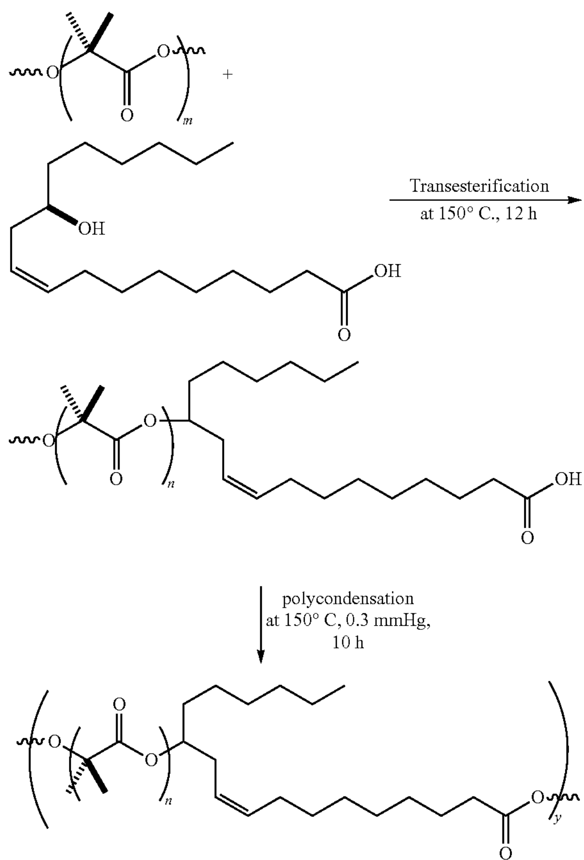

P(LA-RA)s with different PLA block lengths were synthesized by a two-step polycondensation to yield viscous liquid to viscous semi-solid materials (Scheme 2).

Scheme 2.

Synthesis of P(LA-RA)s 80:20 with different PLA chain lengths.

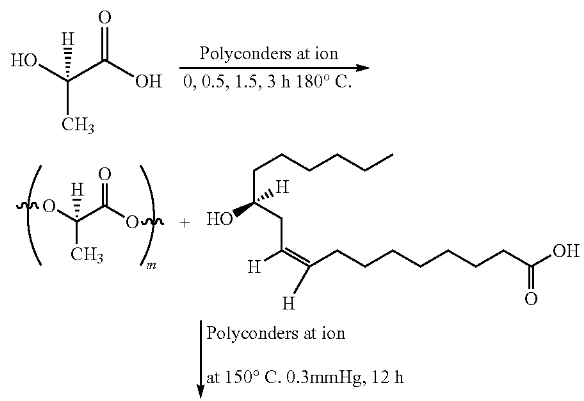

-continued

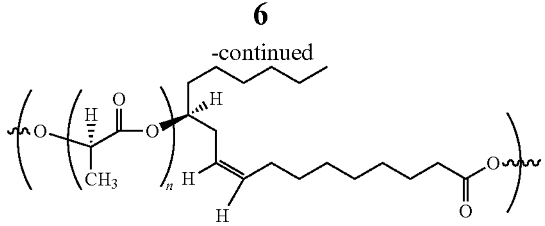

Transesterification of high molecular weight PLA with pure ricinoleic acid and repolymerization of those oligomers by condensation resulted in multiblock P(PLA-RA) copolyesters of molecular weights between 6000 and 40,000. The polymers with 50% RA were liquids at room temperature. $^{1}$H-NMR spectroscopy analysis coupled with information from DSC allowed determination of the polymer structure.

b. Incorporation of the Active Agent into the Polymer Matrix

Controlled release devices are typically prepared in one of several ways. For example, the polymer can be melted, mixed with the active substance and cast or injection molded into a device. Such melt fabrication require polymers having a melting point that is below the temperature at which the substance to be delivered and polymer degrade or become reactive.

The device can be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

III. Method of Use

The polymeric compositions described herein can be used as degradable carriers for treating local diseases such as cancer, bacterial and fungi local infections and pain. For most regional drug delivery, the drug should be administered for a period of weeks to months. Site-specific chemotherapy that provides high drug concentrations for an extended time period in the diseased site is an effective way of treating remnant infected cells after resection of the infected area such as solid tumors. Typically the formulation is administered by injection and/or implantation, intramuscularly, subcutaneously, intraperitoneally, and/or intratumor (before, during or after tumor resection)

Of specific interest is the application of these polymers for site-specific chemotherapy for the treatment of solid tumors including: squamous cell carcinoma (SCC) of the head & neck, prostate cancer, and sarcomas for intratumoral injection or insertion. Cancer of the head and neck accounts for about 40,000 new cases every year in the United States, which is about 5% of all new cancer cases in the United States. Unlike other solid tumors, the most common manifestation of recurrence of head and neck cancer is regional, that is, recurrence in the neck. A prospective device based on the polymers of this invention is a pasty or liquid polymeric implant, made of a biodegradable polymer matrix loaded with an anticancer agent. The anticancer agent, such as Cisplatin or Paclitaxel, is homogeneously dispersed into the polymer matrix. The active drug is released in a controlled manner to the surrounding tissue, when placed in contact with body fluids, while the polymer carrier is eliminating-by slow degradation.

The implant, in a form of an injectable liquid or paste, is injected into the tumor or inserted into the tumor site during the surgical procedure of tumor removal. The implant provides a high dose of anti-cancer drug for an extended period of time, typically days, weeks or months, in the tumor site, with minimal systemic drug distribution, thus, providing a localized treatment of the residual tumor cells as a complementary drug therapy to the surgery.

The same concept of long term drug delivery to specific diseased body sites applies also to other solid tumors, local infections such as osteomyelitis-bone infection, local anesthetic delivery for cancer or AIDS patients and drugs that control tissue growth such as heparin and steroids for treating restenosis and keloids.

EXAMPLES

Materials

Crude ricinoleic acid was purchased from Acros (85% pure) (Geel, Belgium), l-Lactic acid (l-LA) and dl-Lactic acid (dl-LA) were purchased from J. T. Baker [Deventer, Netherlands]. D-Lactic acid was prepared from the hydrolysis of d-Lactide in water. d-Lactide was purchased from Purac Biochem (Gorinchem, Netherlands),. Pure ricinoleic acid (>95% content with the rest is fatty acid mixture) was prepared from the purification of crude ricinoleic acid by chromatography or by precipitation of the potassium salt of ricinoleic acid in ethanol and extraction with solvents such as acetonitrile followed by solvent evaporation. Alternatively, pure ricinoleic acid is prepared by hydrolysis of castor oil in an ethanolic solution of KOH and extraction and acidification with HCl aqueous solution.

Instrumentation

IR spectra were performed on monomer and polymer samples cast on NaCl plates from $CH_2Cl_2$ solutions on a Bruker Vector 22 System FT-IR. UV spectra were taken on a Kontron Instruments Uvicon model 930 (Msscientific. Berlin, Germany).

Thermal analysis was determined on a Mettler TA 4000-DSC differential scanning calorimeter (Mettler-Toledo. Schwerzzenbach, Schweiz), calibrated with Zn and In standards, at a heating rate of 10° C./min under nitrogen atmosphere. Melting temperatures of the co-polyesters was determined also by Fisher Scientific melting point apparatus (USA).

Molecular weights of the co-polyesters were estimated on a gel permeation chromatography (GPC) system consisting of a Waters 1515 Isocratic HPLC Pump, with 2410 Refractive Index detector (RI) (Waters, M A), a Rheodyne (Coatati, Calif.) injection valve with a 20 μL loop. Samples were eluted with chloroform through a linear Styrogel column, 500 Å-pore size (Waters, M A) at a flow rate of 1 mL/min. The molecular weights were determined relative to polystyrene standards (Polyscience, Warrington, Pa.) with a molecular weight range of 500 to 20,000 using BREEZE 3.20 version, copyright 2000 Waters corporation computer program.

The lactic and ricinoleic acids release was determined by HPLC using C18 reverse-phase column (LichroCart® 250-4, Lichrospher® 100, 5 μm). Lactic acid was eluted with a solution of 0.1% $H_3PO_4$ in DDW at a flow rate of 1 ml/min and UV detection at 210 nm. Ricinoleic acid was eluted with a solution of acetonitrile: 0.1% $H_3PO_4$ in DDW 65:35 v/v, at flow rate of 1.4 ml/min and UV detection at 210 nm.

The hydrolysis was conducted in 0.1M phosphate buffer (pH 7.4) at 37° C. with a constant shaking of 100 rpm. $^1$H-NMR and $^{13}$C-NMR spectra (in $CDCl_3$) were recorded on a Varian 300 MHz and 500 MHz spectrometers using TMS as internal standard (Varian Inc., Palo Alto, Calif.). Optical rotations of polymers were determined by an Optical Activity LTD polarimeter (Cambridgeshire, England) using 10 mg/ml polymer solutions in $CHCl_3$. Viscometry of the polymers in dichloromethane was measured in Cannon-Ubbelohde 75 micrometer dilution viscometer. Afflux times were measured at four concentrations at 25° C., and the data was analyzed by standard methods.

Example 1

Synthesis of Poly(Ricinoleic-Lactic Ester) by Thermal Condensation

P(l-LA:RA) and P(d-LA:RA) with different LA:RA (w/w) ratios were prepared by two step thermal polycondensation according to the following procedure.

A 250 mL round-bottomed flask, equipped with a dean-stark trap, a reflux condenser and a $CaCl_2$ drying tube was charged with pure ricinoleic acid and leophylized lactic acid in appropriate ratios (total amount of both acids was 20 g) and 150 ml of Toluene.

The acid mixture was dried overnight with refluxing toluene to remove trace amount of water. The toluene was removed and the temperature was raised gradually to 180° C. The acids were condensed for 3 hours. In the second step, the temperature was decreased to 150° C. and the reaction flask was connected to an oil pump where the condensation was continued under a vacuum of 0.3 mmHg for an additional 12 hours. Each step was followed by GPC analysis of samples to determine the molecular weight of the forming polymers at each time period. All polymers were characterized by GPC, $^1$H-NMR, IR, DSC, m.p, Cannon-Ubbelolohde 75 dilution viscometer and specific optical rotation.

$^1$H-NMR ($CDCl_3$, P(LA-RA) 60:40, δ): 5.45-5.30 (2H, m, C9-10, —CH═CH—), 5.20-5.02 (1H, q, CH—CH3, LA), 4.94-4.86 (1H, m, C12 HC—O—), 2.38-2.24 (2H, m C2 —$CH_2$, and 2H, m, C11 —$CH_2$), 2.01 (2H, m, C8 —$CH_2$), 1.68-1.50 (2H, m, C3 —$CH_2$, 2H, m, C13 —$CH_2$, and 3H, d, —CH3, LA), 1.34-1.25 (16H, m, C4-7 and C14-17) and 0.868 (3H, t, C18 —CH3) ppm.

$^1$H-NMR ($CDCl_3$, 100% PRA, δ): 5.44-5.30 (2H, m, C9-10, —CH═CH—), 4.873 (1H, m, C12 HC—O—), 2.309 (2H, t, C2 —$CH_2$), 2.194 (2H, t, C11 —$CH_2$), 2.01 (2H, m, C8 —$CH_2$), 1.603 (2H, m, C3—$CH_2$), 1.446 (2H, m, C13 —$CH_2$), 1.291 (16H, m, C4-7 and C14-17) and 0.862 (3H, t, C18 —$CH_3$) ppm. $^1$H-NMR ($CDCl_3$, PLA, δ): 5.16-5.15 (1H, q, CH—CH3), 1.58-1.56 (3H, d, —CH3, LA) ppm.

Polymers with molecular weights in the range 2000 to 11000 were obtained. All polymers possess typical IR absorption at 1748 $cm^{-1}$ corresponding to the ester carbonyl stretching bands. $^1$H NMR spectra of the polymers fit their composition. The molecular weights, thermal properties, specific optical rotation of the polymers, and their intrinsic viscosity are summarized in Table 1. Copolymerization processes did not affect the optical purity of the PLAs. There is correlation between intrinsic viscosity and P(LA-RA) molecular weight and content. All the liquid polymers had an intrinsic viscosity (in dichloromethane) between 0.10 and 0.16 dL/g (Table 1). Solid polymers were found to be more viscous in the same conditions. All P(LA:RA)s with up to 20% RA w/w had an intrinsic viscosity between 0.14 and 0.27 dL/g. RA and LA acids were condensed at 180° C. for 3 hours.

TABLE 1

Physical Properties of P(LA:RA) Copolymers Synthesized by Thermal Condensation

| Polymer[(a)], P(LA:RA), w/w | Lactic Acid[(b)] | Specific Optical Rotation[(c)], $[\alpha]^{20}_D$ | Melting Points[(d)], ° C. | Intrinsic Viscosity[(e)], dL/g | Molecular Weight[(f)] |
|---|---|---|---|---|---|
| 80:20 | L | −106 | Liquid | 0.11 | 4200 |
| 70:30 | L | −94 | Liquid | 0.16 | 7800 |
| 60:40 | L | −93 | Liquid | 0.13 | 5500 |
| 50:50 | L | −88 | Liquid | 0.13 | 4500 |

Legend for Table 1:

RA and LA acids were condensed at 180° C. for 3 hours

[(a)]w/w ratio of the monomers used for copolymerization;

[(b)]lactic acid type;

[(c)]optical rotations of polymers determined by Optical Activity LTD polarimeter in 10 mg/ml polymer solution in CHCl3;

[(d)]melting temperature of the copolymers measured by Fisher apparatus;

[(e)]intrinsic viscosity of the polymers in dichloromethane measured in Cannon-Ubbelohde 75 dilution visometer;

[(f)]molecular weight determined by GPC.

Example 2

Synthesis of Poly(Ricinoleic-Lactic Ester) by Tranesterification and Repolymerization by Polycondensation A 250 mL round-bottomed flask, equipped with dean-stark, reflux condenser and $CaCl_2$ drying tube was charged with pure ricinoleic acid and PLA (L-PLA: Mn=41,000; Mw=91,000) in desired ratios (w/w total amount of both compounds was 10 g) and 100 ml toluene. The ingredients were dried overnight by refluxing toluene to remove trace amounts of water. Toluene was removed and transesterification proceeded for 12 hours at 150° C., followed by GPC and $^1$H-NMR analysis. The reaction was stopped as soon as the product achieved minimal constant molecular weight.

Repolymerization was carried-out by thermal polycondensation. The reaction flask was connected to an oil pump and heated to 150° C. under a vacuum of 0.3 mmHg for additional 10 hours, followed by GPC. All polymers were characterized by GPC,1H-NMR, IR, DSC, m.p, Cannon-Ubbelolohde 75 dilution viscometer and specific optical rotation.

$^1$H-NMR (P(LA-RA) 60:40, δ): 5.47-5.29 (2H, m, C9-10, —CH═CH—), 5.20-5.00 (1H, q, CH—CH3, LA), 4.90-4.87 (1H, m, C12 HC—O—), 2.38-2.24 (2H, m, C2 —$CH_2$, and 2H, m, C11 —$CH_2$), 1.99 (2H, m, C8 —$CH_2$), 1.66-1.40 (2H, m, C3 —$CH_2$, 2H, m, C13 —$CH_2$, and 3H, d, —CH3, LA), 1.30-1.24 (16H, m, C4-7 and C14-17) and 0.866 (3H, t, C18 —$CH_3$).

The molecular weight after 12 hours of transesterification fit the expected molecular weight reduction. At this stage, the system was connected to a high vacuum oil pump and repolymerization process started. The repolymerization condensation was continued until no additional increase in polymer's molecular weight was observed. It was found that for all PLA:RA ratio AAAAB blocks were connected during repolymerization reaction. The molecular weights and melting temperatures of the P(PLA-RA) are shown in Table 2. Polymers with molecular weights in the range of 5000 to 11000 were obtained. There is a correlation between intrinsic viscosity and the P(LA-RA)s molecular weight.

TABLE 2

Physical Properties of P(LA:RA) Copolymers Synthesized by Transesterification and Repolymerization

| Polymer[(a)], P(l-P(LA:RA), w/w | Specific Optical Rotation[(b)], $[\alpha]^{20}_D$ | Melting Points[(c)], ° C. | Intrinsic Viscosity[(d)], dL/g | Molecular Weight[(e)]: 12 Hours transesterification 150° C. Mn | 12 Hours transesterification 150° C. Mw | 10 hours repolymerization 150° C., 0.3 mmHg Mn | 10 hours repolymerization 150° C., 0.3 mmHg Mw |
|---|---|---|---|---|---|---|---|
| 100% l-PLA | −140 | 162 | 0.25 | 2400 | 3000 | 11000 | 13000 |
| 90:10 | −130.5 | 147 | 0.24 | 3200 | 4700 | 11000 | 14000 |
| 80:20 | −106 | 142 | 0.14 | 1800 | 4000 | 5000 | 8000 |
| 70:30 | −81 | 111 | 0.15 | 1500 | 2600 | 5500 | 8100 |
| 60:40 | −68 | 93 | 0.13 | 1300 | 2200 | 5000 | 7000 |
| 50:50 | −38 | Liquid at room temp | 0.15 | 1200 | 2000 | 5600 | 8200 |
| 100% PRA | +25.5 | Liquid at room temp | 0.10 | 1400 | 2000 | 4300 | 5600 |

Legend for Table 2:

Polymers synthesized by transesterification of L-PLA Mw = 91,000 with RA at 150° C. and repolymerization

[(a)]w/w ratio of the monomers used for copolymerization;

[(b)]optical rotations of polymers determined by Optical Activity LTD polarimeter in 10 mg/ml polymer solution in CHCl3;

[(c)]melting temperature of the copolymers measured by Fisher apparatus;

[(d)]intrinsic viscosity of the polymers in dichloromethane measured in Cannon-Ubbelohde 75 dilution viscometer;

[(e)]molecular weight determined by GPC.

DSC revealed crystalline structure for polyester synthesized by transesterification and by ROP (FIG. 1). For polyesters synthesized by random condensation only P(LA-RA) 90:10 w/w contained crystalline areas. This information is correlated with the 1H-NMR analysis where polymers containing relatively long LA blocks obtain crystallize areas. In P(LA-RA)s, only LA blocks are able to crystallize. Ricinoleic acid structure is sterrically hindered where RA blocks form non-crystalline brushlike domains along the polymer chain, thus increasing the RA content decreased the melting point and the crystallinity of the polymers. FIG. 1 shows the crystalline structure, as determined by DSC, for different polyhydroxyalkanoic acid polyesters synthesized by transesterification and ring-opening polymerization (ROP): (a) 100% PLA; (b) P(LA-RA) 90:10 w/w; (c) P(LA-RA) 80:20 w/w; (d) P(LA-RA) 70:30 w/w; (e) P(LA-RA) 60:40 w/w; (f) P(LA-RA) 50:50 w/w. Graphs 1 and 3 in FIG. 1 show that polymers possessing sufficiently long LA blocks form detectable crystalline domains in the polymer. In contrast, Graphs 2*c-f* in FIG. 1 show that copolymers with an RA content of at least 20% do not have LA blocks long enough to form detectable crystalline area in the polymer.

Stereocomplexation

L-lactic acid and ricinoleic acid based copolyesters were synthesized by melt condensation and transesterification of high molecular weight poly(lactic acid) (PLA) with ricinoleic acid and repolymerization by condensation to yield random and block copolymers of molecular weights between 3,000 and 6,000. In order to correlate between the copolyesters synthesized by polycondensation and transesterification, P(LA-RA)s with different PLA blocks were synthesized. The relative degree of crystallinity of those copolyesters depends directly on the PLA block size, which is the only difference between the corresponding polymers. 1H-NMR spectroscopy analysis coupled with information from DSC allowed correlation between the degree of crystallinity and PLA block size.

P(l-LA-RA)s and corresponding enantiomeric d-PLA were mixed together in acetonitrile solution to form stereocomplexes. Stereocomplex formation was dependant on the size of PLA block in the P(l-LA-RA)s, with block length of at least 10 LA units required to form a stereocomplex. The formed stereocomplexes exhibited higher crystalline melting temperature than the enantiomeric polymers, which indicate stereocomplex formulation.

Example 3

Synthesis of Poly(Ricinoleic-Lactic Ester) by Ring Opening Polymerization (ROP)

Copolyesters of LA-RA with different LA:RA ratios were prepared by ring opening polymerization (ROP). A solution of l-Lactide (LA) and Ricinoleic acid lactone (RA) was dried by evaporating the toluene over 4 hours. Tin octanoate (Sn (Oct), 60 mg) was added as a catalyst, and the solution was allowed to react at 135° C. After 4 hours a sample was removed for molecular weight determination. The reaction was stopped after 24 hours and the molecular weight of the polymer formed was determined. All polymers were characterized by 1H-NMR, GPC, IR, DSC and specific optical rotation.

1H-NMR (50% L-PLA-RA, δ): 5.45-5.33 (2H, m, C9,C10, —CH═CH—), 5.19-5.12 (1H, q, CH—CH3, LA), 4.93-4.89 (1H, m, C12 HC—O—), 3.66-3.58(1H, m, —CH—OH, RA) 2.28-2.227 (2H, m, C2 —CH2, and 2H, m, C11 —CH2), 2.01 (2H, m, C8 —CH2), 1.68-1.50 (2H, m, C3 —CH2, 2H, m, C13 —CH2, and 3H, d, —CH3, LA), 1.34-1.29 (16H, m, C4-7 and C14-17) and 0.865 (3H, t, C18 —CH3).

Example 4

Synthesis of Poly(Ricinoleic-Lactic Ester) with Different PLA Chain Lengths

Low molecular weight polyesters, P(l-LA:RA) 80:20 with different size, time-dependent LA blocks were prepared by a two step thermal polycondensation according to the following procedure:

A 250 mL round-bottomed flask, equipped with a dean-stark apparatus, reflux condenser and CaCl2 drying tube, was charged with 16 g lyophilized l-lactic acid and 150 ml toluene. The lactic acid solution was dried overnight with refluxing toluene to remove water traces, then the toluene was removed and the temperature was raised gradually to 180° C. The reaction was continued for 0.5, 1.5 and 3 hours to obtain different size PLA blocks. The molecular weight of the forming polymers was determined by GPC.

In the second step, 4 g of pure, dry ricinoleic acid was dissolved in 50 ml toluene and was added to the PLA flasks. Toluene was removed and the temperature was raised gradually to 180° C. The reaction was continued for 4 hours and then connected to an oil pump where the condensation was continued under a vacuum of 0.3 mmHg for additional 12 hours. Each step was followed by GPC analysis of samples removed from the reaction flasks to determine the molecular weight of the forming polymers at each time period. All polymers were characterized by GPC, 1H-NMR, IR, DSC and specific optical rotation.

1H-NMR (CDCl3, P(LA-RA) 1.5 h prepolymerization; 80:20, δ): 5.45-5.30 (2H, m, C9-10, —CH═CH—), 5.20-5.02 (1H, q, CH—CH3, LA), 4.94-4.86 (1H, m, C12 HC—O—), 2.38-2.24 (2H, m, C2 —CH2, and 2H, m, C11 —CH2), 2.01 (2H, m, C8 —CH2), 1.68-1.50 (2H, m, C3 —CH2, 2H, m, C13 —CH2, and 3H, d, —CH3, LA), 1.34-1.25 (16H, m, C4-7 and C14-17) and 0.868 (3H, t, C18 —CH3)ppm.

Polymers with molecular weights in the range of 3000 to 5000 were obtained. All polymers possess typical IR absorption at 1748 $cm^{-1}$ corresponding to the ester carbonyl stretching bands. The molecular weights, thermal properties, specific optical rotation of the polymers, and their intrinsic viscosity are summarized in Table 3. There was a correlation between the intrinsic viscosity and P(LA-RA) molecular weight.

TABLE 3

Physical Properties of P(LA:RA) Copolymers with Different PLA Chain Lengths

| Initial PLA Block Length | | | | | | | | |
|---|---|---|---|---|---|---|---|---|
| Molecular Weight | | | Intrinsic Viscosity[c], | Specific Optical Rotation[d], | Melting Point, Karl-Fisher[e], | Melting Range DSC[f], | Molecular | |
| Mn | Mw | $L_{(la)}$[b] | dL/g | $[\alpha]^{20}_D$ | ° C. | ° C. | Weight[a] | |
| 72 | 72 | 1 | 0.14 | −106 | Liquid at room Temp. | Liquid at room temp. | 2500 | 3200 |
| 550 | 650 | 9 | 0.15 | −109 | 55-60 | 90 | 2500 | 4900 |
| 730 | 850 | 12 | 0.14 | −111 | 65-70 | 105 | 1900 | 3600 |
| 1000 | 1400 | 20 | 0.16 | −118 | 75-80 | 110 | 3100 | 5300 |

Legend for Table 3:

Polymers synthesized by polycondensation of RA with LA oligomers prepared by condensation of LA;

[a]molecular weight of initial LA oligomers and P(LA-RA) determined by GPC;

[b]initial PLA block length L(la) = Mw(PLA)/Mw(la);

[c]intrinsic viscosity of the polymers in dichloromethane measured in Cannon-Ubbelohde 75 dilution viscometer;

[d]optical rotation was determined by Optical Activity LTD polarimeter using 10 mg/ml polymer solution in chloroform;

[e]melting temperatures of the copolymers measured by Fischer apparatus;

[f]melting range of the copolymers measured by DSC.

Stereocomplex Preparation

Stereocomplexes were prepared by mixing the acetonitrile solutions of the enantiomers and collecting the precipitated stereocomplexes. Stereocomplex formation was tested for all P(LA-RA)s synthesized by transesterification, polycondensation and polycondensation with initial PLA blocks. In a typical experiment, P(l-LA-RA) 70:30 (500 mg) having a number average molecular weight of 5800 and d-PLA (350 mg) (1:1 w/w ratio of PLAs) having a number average molecular weight of 3000 were dissolved separately in acetonitrile (2 ml). The solutions were mixed together for 4 min by vortex apparatus followed by mixing at 37° C. for an additional 4 hours at 100 r/min. The solutions were left at room temperature without stirring overnight. The stereocomplex powder was collected by filtration. The filtrate was poured onto a glass Petry dish to allow solvent evaporation. The precipitates were characterized by DSC and SEM.

Example 5

Hydrolytic Degradation and Drug Release of Ricinoleic Acid Based Co-Polyesters a. Degradation of Ricinoleic Acid Based Co-Polyesters L-lactic acid and ricinoleic acid based copolyesters were synthesized by ring opening polymerization, melt condensation and transesterification (as described in the previous examples) of high molecular weight poly(lactic acid) (PLA) with ricinoleic acid and repolymerization by condensation to yield random and block copolymers of molecular weights between 3,000 and 13,000.

The lactic and ricinoleic acids release was determined by HPLC using C18 reverse-phase column (LichroCart® 250-4, Lichrospher® 100, 5 μm). Lactic acid was eluted with a solution of 0.1% $H_3PO_4$ in DDW at a flow rate of 1 ml/min and UV detection at 210 nm. Ricinoleic acid was eluted with a solution of acetonitrile: 0.1% $H_3PO_4$ in DDW 65:35 v/v, at a flow rate of 1.4 ml/min and UV detection at 210 nm. The hydrolysis was conducted in 0.1M phosphate buffer (pH 7.4) at 37° C. with a constant shaking of 100 rpm. Triamcinalone and 5FU concentrations in solution during drug release, were determined by UV detection at 242 nm and 267 nm, respectively. 1H-NMR and 13C-NMR spectra (in $CDCl_3$) were recorded on a Varian 300 MHz and 500 MHz spectrometers using TMS as internal standard (Varian Inc., Palo Alto, Calif.). Optical rotations of polymers were determined on an Optical Activity LTD polarimeter (Cambridgeshire, England) using 10 mg/ml polymer in $CHCl_3$ solution. Viscosity of the polymers in dichloromethane was measured in a Cannon-Ubbelohde 75 micrometer dilution viscometer. Afflux times were measured for four concentrations at 25° C., the data were analyzed for viscosity data by standard methods.

Figure 3:
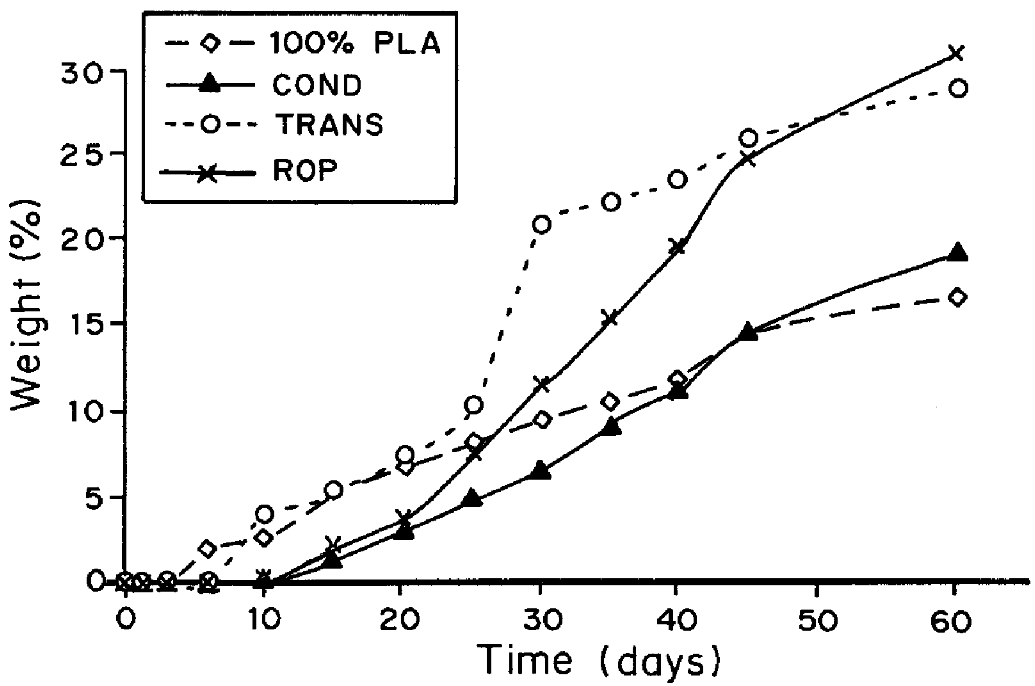
FIG. 3 is a graph which shows % release of lactic acid (LA) to the buffer medium as determined by HPLC as a function of time (days).
Figure 4:
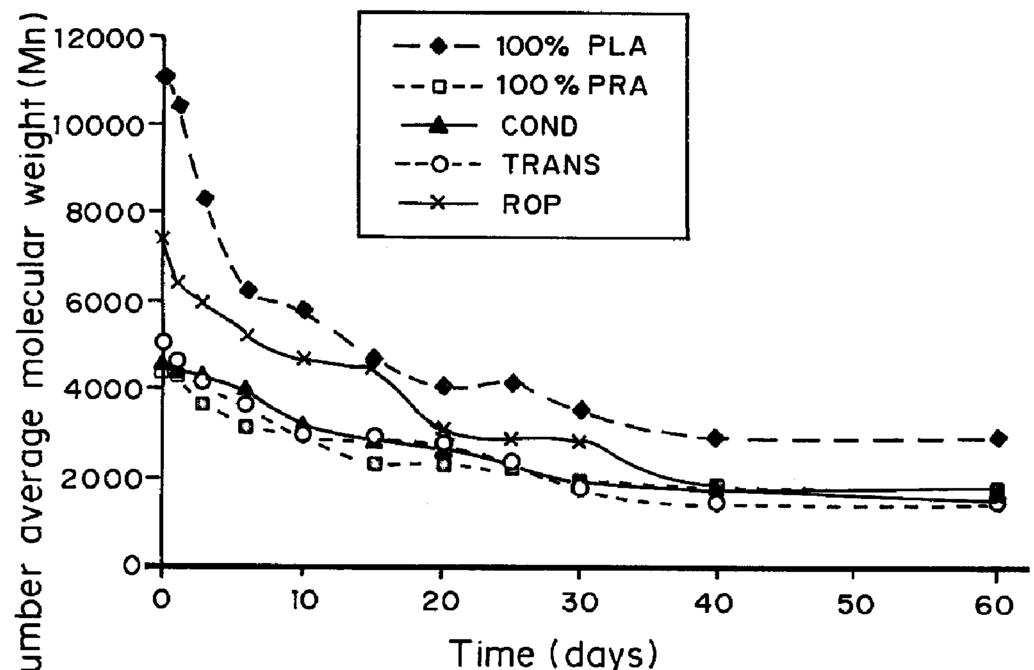
FIG. 4 is a graph which shows Mn loss of P(LA:RA) 60:40 (w/w) as determined by GPC as a function of time (days).

The hydrolysis of the copolyester was evaluated by placing cubic samples of each solid copolyester (3×3×3 mm, 70 mg) in 10 mL 0.1 M phosphate buffer pH 7.4 at 37° C. with constant shaking (100 rpm). The liquid polymers were injected into the phosphate buffer solution (~70 mg of each polymer) for in vitro degradation studies. To avoid saturation of the solution, the phosphate buffer solution was replaced periodically with a fresh buffer solution. At each time point, a polymer sample was taken out of the buffer and vacuum dried at room temperature overnight. The hydrolysis of the polymer was monitored by weight loss of the sample (FIG. 2), release of lactic acid (FIG. 3), and change in polymer molecular weight as determined by GPC (FIG. 4).

Figure 2:
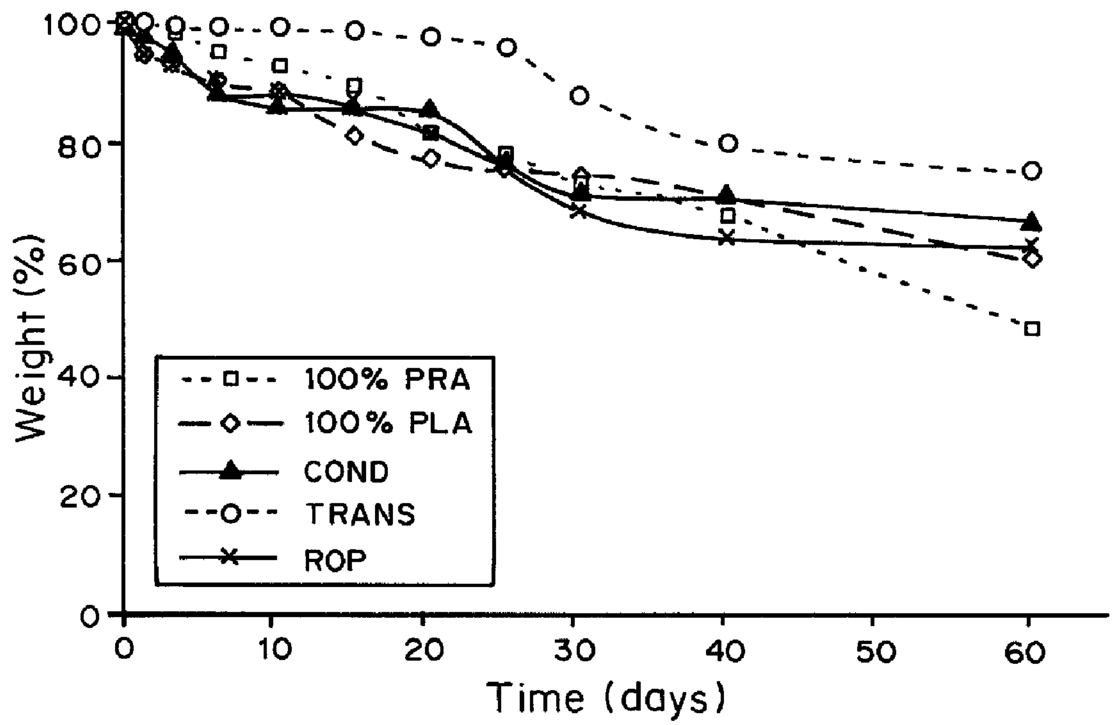
FIG. 2 is a graph which shows % sample weight loss of P(LA:RA) 60:40 (w/w) due to hydrolysis as a function of time (days).

FIG. 2 shows that all polymers exhibited an almost zero-order weight loss, with a 20-40% loss after 60 days of incubation. FIG. 3 shows that lactic acid release to the degradation solution is proportional to the weight loss of the polymer samples. FIG. 4 shows the main decrease in molecular weight was observed during the first 20 days, followed by a slow degradation phase which kept the Mn at 4000-2000 for another 40 days.

b. Drug Release from Ricinoleic Acid Based Co-Polyesters

Figure 5:
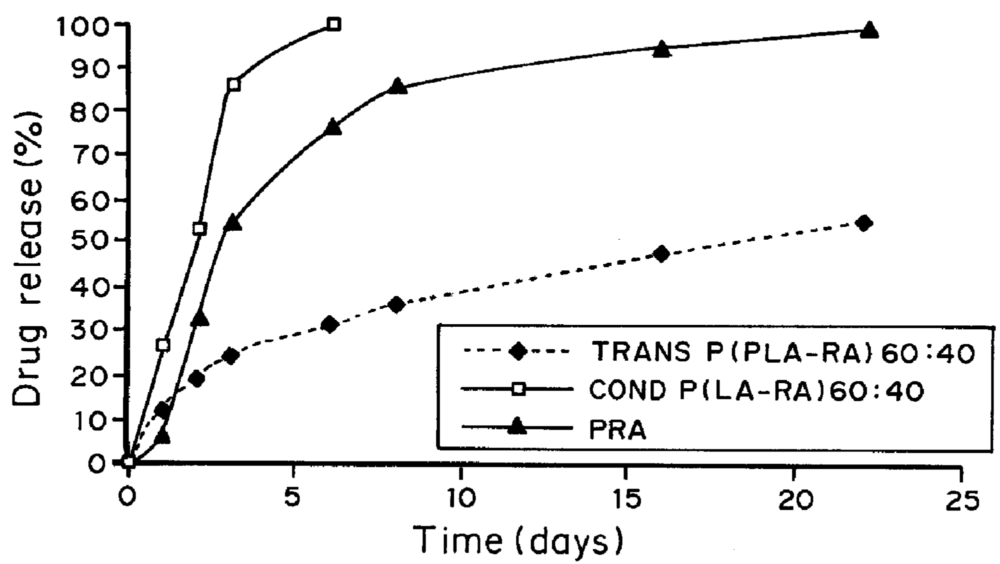
FIG. 5 is a graph which shows the % in vitro release of triamcinalone from P(LA:RA) 60:40 (w/w) and PRA matrices as determined by UV detection as a function of time (days).
Figure 6:
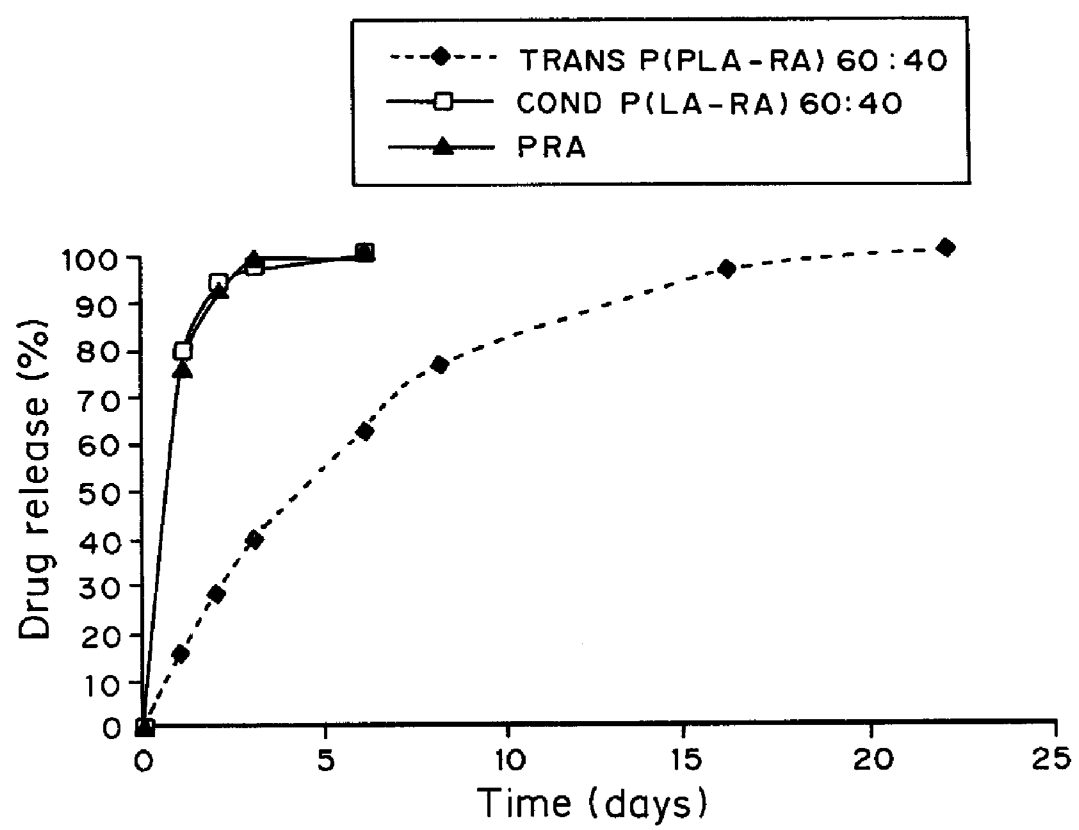
FIG. 6 is a graph which shows the % in vitro release of 5FU from P(LA:RA) 60:40 (w/w) and PRA matrices as determined by UV detection as a function of time (days).

Triamcinalone and 5FU (10 wt %) were incorporated in the P(l-LA-RA)s and PRA by mixing the drug in the polymer melt and then injecting the viscous melt (~70mg) into 100 mL buffer phosphate solution (0.1 M, pH 7.4). Drug release studies were conducted in phosphate buffer (0.1M, pH 7.4) at 37° C. with continuous shaking (100 rpm). At each time point, the solution was replaced with a fresh buffer and drug-analysis was performed. Triamcinalone and 5FU concentrations in the solution were determined by UV detection at 242 nm and 267 nm, respectively. The release of triamcinalone and 5FU is shown in FIGS. 5 and 6. The release of triamcinalone and 5FU is faster from the liquid PRA and condensated P(LA-RA) 60:40 then from pasty P(PLA-RA) 60:40, synthesized by transesterification.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. An injectable or implantable biodegradable polymeric formulation consisting of (a) an active agent and (b) at least one pharmaceutically acceptable excipient for injection or implantation comprising a stereocomplex comprising a biodegradable polyhydroxyalkanoic acid polyester consisting of at least one unsaturated hydroxy fatty acid monomer and at least one hydroxyalkanoic acid or polyhydroxyalkanoic acid monomer, wherein the active agent is dispersed or dissolved in the pharmaceutically acceptable excipient, and wherein the formulation increases in viscosity when injected or implanted into tissue to form a semisolid at the site of injection, and releases the active agent over an extended period of time.

2. The formulation of claim 1, wherein the one or more active agents are selected from the group consisting of bioactive agents, diagnostic agents, and prophylactic agents.

3. The formulation of claim 1, wherein the hydroxyalkanoic acid or polyhydroxyalkanoic acid comprises a hydroxyalkanoic acid having from 2-6 carbon atoms.

4. The formulation of claim 3, wherein the hydroxyalkanoic acid is selected from the group consisting of lactic acid, glycolic acid, 4-hydroxybutanoic acid, and 5-hydroxypentanoic acid.

5. The formulation of claim 1, wherein the unsaturated hydroxy fatty acid is ricinoleic acid.

6. The formulation of claim 1, wherein the at least one pharmaceutically acceptable excipient further comprises surfactants, plasticizers, pigments, colorants, stabilizing agents, or glidants.

7. The formulation of claim 5, wherein the ricinoleic acid has a purity of at least 95%.

8. The formulation of claim 1, wherein the active agent is released over a period of time from about 5 days to about 3 months.

9. The formulation of claim 1, wherein the polymeric formulation is coated, the coating selected from the group consisting of sustained released coatings, delayed release coatings, enteric coatings, and combinations thereof.

10. The formulation of claim 1, wherein the formulation is administered via injection or implantation.

11. The formulation of claim 1, wherein the formulation is injected or implanted intramuscularly, subcutaneously, intraperitoneally, intratumorally, or combinations thereof.

12. The formulation of claim 1, wherein the hydroxyalkanoic acid is lactic acid and the unsaturated hydroxy fatty acid is ricinoleic acid.

13. The formulation of claim 12, wherein the polyhydroxyalkanoic acid polyester has an average molecular weight of from 3,000 to 40,000 Daltons.

14. The formulation of claim 13 , wherein the polyhydroxyalkanoic acid polyester has a molecular weight of from 3,000-13,000 Daltons.

15. The formulation of claim 14, wherein the polyhydroxyalkanoic acid polyester has a molecular weight from 5,000-11,000 Daltons.

16. The formulation of claim 13, wherein the polyhydroxyalkanoic acid polyester has an average molecular weight of from 6,000 to 40,000 Daltons.

* * * * *